United States Patent
Yonce et al.

(10) Patent No.: US 9,662,491 B2
(45) Date of Patent: May 30, 2017

(54) TIBIAL NERVE STIMULATION DEVICE

(71) Applicant: Astora Women's Health, LLC, Eden Prairie, MN (US)

(72) Inventors: David J. Yonce, Malvern, PA (US); John Jason Buysman, Minnetonka, MN (US); Richard A. Lundeen, Eden Prairie, MN (US); Jeffrey John Childs, Eagan, MN (US)

(*) Notice: Subject to any disclaimer, the term of this patent is extended or adjusted under 35 U.S.C. 154(b) by 0 days.

(21) Appl. No.: 14/996,869

(22) Filed: Jan. 15, 2016

(65) Prior Publication Data
US 2016/0129250 A1 May 12, 2016

Related U.S. Application Data

(63) Continuation of application No. 14/342,592, filed as application No. PCT/US2012/053903 on Sep. 6, 2012, now Pat. No. 9,265,927.

(60) Provisional application No. 61/532,744, filed on Sep. 9, 2011.

(51) Int. Cl.
| | |
|---|---|
| *A61N 1/36* | (2006.01) |
| *A61N 1/04* | (2006.01) |
| *A61N 1/378* | (2006.01) |
| *A61N 1/372* | (2006.01) |

(52) U.S. Cl.
CPC ....... *A61N 1/36017* (2013.01); *A61N 1/0456* (2013.01); *A61N 1/0484* (2013.01); *A61N 1/36007* (2013.01); *A61N 1/36021* (2013.01); *A61N 1/36071* (2013.01); *A61N 1/36157* (2013.01); *A61N 1/372* (2013.01); *A61N 1/378* (2013.01)

(58) Field of Classification Search
None
See application file for complete search history.

(56) References Cited

U.S. PATENT DOCUMENTS

| | | |
|---|---|---|
| 6,735,474 B1 | 5/2004 | Loeb et al. |
| 2005/0264979 A1 | 12/2005 | Breyen et al. |
| 2008/0208287 A1* | 8/2008 | Palermo ............... A61N 1/0452 607/48 |

(Continued)

FOREIGN PATENT DOCUMENTS

| | | |
|---|---|---|
| GB | 1 392 439 A | 4/1975 |
| WO | 2013036599 A1 | 3/2013 |

OTHER PUBLICATIONS

Patent Examination Report No. 1 dated Feb. 18, 2016 from corresponding Australian Patent Application No. 2012304638, filed Feb. 19, 2014.

(Continued)

*Primary Examiner* — Carl H. Layno
*Assistant Examiner* — Ankit D Tejani
(74) *Attorney, Agent, or Firm* — Brake Hughes Bellermann LLP

(57) ABSTRACT

A stimulation therapy device provides an electrical stimulation therapy to branches of the tibial nerve of a patient. The device comprises a support member configured to be worn around the ankle or foot of the patient, first and second pairs of electrodes attached to the support member, and a stimulation circuit attached to the support member. The stimulation circuit is configured to deliver electrical stimulation pulses through the first and second pairs of electrodes.

10 Claims, 3 Drawing Sheets

(56) References Cited

U.S. PATENT DOCUMENTS

| | | |
|---|---|---|
| 2009/0054952 A1 | 2/2009 | Glukhovsky et al. |
| 2009/0076565 A1 | 3/2009 | Surwit |
| 2009/0082835 A1 | 3/2009 | Jaax et al. |
| 2009/0326602 A1 | 12/2009 | Glukhovsky et al. |
| 2011/0021863 A1 | 1/2011 | Burnett et al. |
| 2011/0301670 A1 | 12/2011 | Gross et al. |
| 2014/0257436 A1 | 9/2014 | Yonce et al. |

OTHER PUBLICATIONS

EPO Communication from European Application No. 12762135.7 mailed May 9, 2014.

Urgent® PC Neuromodulation System, Brochure, Uroplasty, Inc. www.urgentpcinfo.com (2005) Uroplasty, Inc. 2 pgs.

International Search Report and Written Opinion from corresponding PCT/US2012/053903, mailed Nov. 19, 2012.

Pulsed Electromagnetic Stimulation for Treatment of Overactive Bladder, retrieved from http://clinicaltrials.gov/ct2/show/NCT00805779 on Aug. 15, 2011, 5 pages.

First communication issued by the European Patent Office for EP Patent Application No. 12 762 135.7, dated Apr. 14, 2015.

Prosecution History from U.S. Appl. No. 141342,592 including: Non-Final Office Action mailed Feb. 19, 2015; and Final Office Action mailed Jun. 11, 2015.

* cited by examiner

TIBIAL NERVE STIMULATION DEVICE

CROSS-REFERENCE TO RELATED APPLICATION

This Application is continuation of U.S. patent application Ser. No. 14/342,592, filed May 6, 2014, which is a Section 371 National Stage Application of International Application No. PCT/US2012/053903, filed Sep. 6, 2012 and published as WO 2013/036599 A1 on Mar. 14, 2013 in English, and claims the benefit of U.S. Provisional Application Ser. No. 61/532,744, filed Sep. 9, 2011 under 35 U.S.C. §119(e). The above-referenced applications are hereby incorporated by reference in their entirety.

FIELD

Embodiments of the invention are directed to a stimulation therapy device and method for stimulating branches of nerves in the tibial area of a patient. This stimulation can be used to treat a pelvic condition of a patient, such as overactive bladder or urge incontinence, for example.

BACKGROUND

The tibial nerve is a branch of the sciatic nerve that passes alongside the tibia and into the foot. At the ankle, the tibial nerve is relatively close to the surface of the skin. Stimulation of the tibial nerve can be used to treat urinary incontinence, fecal incontinence, pelvic pain, and other conditions.

These stimulation treatments typically involve the use of a percutaneous electrode or device that is inserted into the subject's ankle. For instance, U.S. Pat. No. 6,735,474 (Loeb et al.) discloses the use of micro-stimulators that are inserted beneath the skin of the perineum and/or adjacent the tibial nerve to treat incontinence, pelvic pain, and fecal incontinence. U.S. Publication No. 2011/0301670 (Gross et al.) discloses the use of percutaneous electrodes that are placed in contact with the tibial nerve to deliver electrical stimulation signals to the nerve to treat polyneuropathy. Uroplasty Inc. (Minnesota, USA) manufactures the Urgent® PC Neuromodulation System, which delivers electrical stimulation to the tibial nerve using a percutaneous needle electrode to treat urinary urgency, urinary frequency (i.e., overactive bladder), and urge incontinence.

SUMMARY

Embodiments of the invention are directed to a stimulation therapy device that is configured to provide an electrical stimulation therapy to branches of the tibial nerve of a patient. In one embodiment, the device comprises a support member configured to be worn around the ankle or foot of the patient, first and second pairs of electrodes attached to the support member, and a stimulation circuit attached to the support member. The stimulation circuit is configured to deliver electrical stimulation pulses through the first and second pairs of electrodes.

Another embodiment of the invention is directed to a method of applying an electrical stimulation therapy to branches of the tibial nerve of a patient. In the method, first and second pairs of electrodes are positioned on the ankle area of the patient. Electrical stimulation pulses are delivered to branches of the tibial nerve through the first and second pairs of electrodes. In one embodiment, the delivery of the electrical stimulation pulses involves discharging a first stimulation pulse through the first pair of electrodes, and discharging a second stimulation pulse through the second pair of electrodes after discharging a first stimulation pulse.

This Summary is provided to introduce a selection of concepts in a simplified form that are further described below in the Detailed Description. This Summary is not indented to identify key features or essential features of the claimed subject matter, nor is it intended to be used as an aid in determining the scope of the claimed subject matter. The claimed subject matter is not limited to implementations that solve any or all disadvantages noted in the Background.

DETAILED DESCRIPTION OF ILLUSTRATIVE EMBODIMENTS

Figure 1:
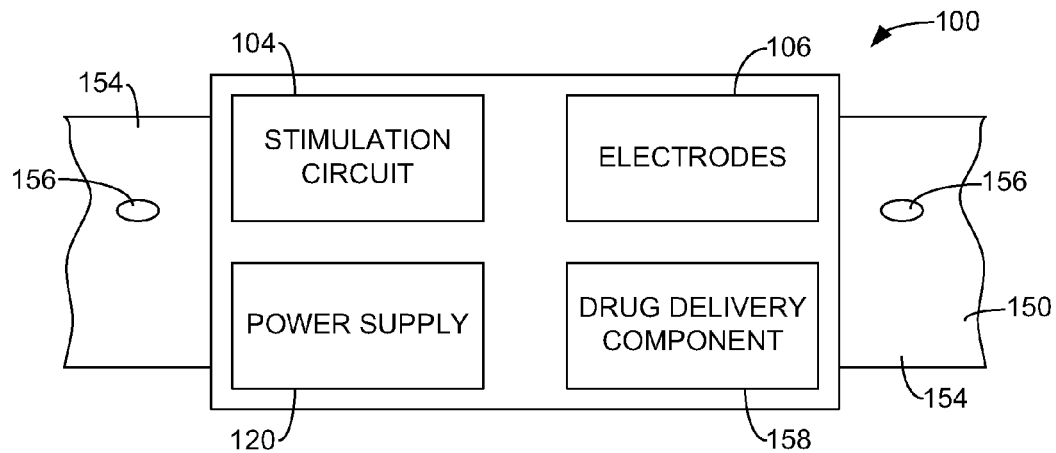
FIG. 1 is a block diagram of a stimulation therapy device in accordance with embodiments of the invention.

Embodiments of the invention are described more fully hereinafter with reference to the accompanying drawings. The various embodiments of the invention may, however, be embodied in many different forms and should not be construed as limited to the embodiments set forth herein. Rather, these embodiments are provided so that this disclosure will be thorough and complete, and will fully convey the scope of the invention to those skilled in the art. Elements that are identified using the same or similar reference characters refer to the same or similar elements.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It will be understood that when an element is referred to as being "connected" or "coupled" to another element, it can be directly connected or coupled to the other element or intervening elements may be present. In contrast, if an element is referred to as being "directly connected" or "directly coupled" to another element, there are no intervening elements present.

It will be understood that, although the terms first, second, etc. may be used herein to describe various elements, these elements should not be limited by these terms. These terms are only used to distinguish one element from another. Thus, a first element could be termed a second element without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As will further be appreciated by one of skill in the art, the present invention may be embodied as methods, systems, and/or computer program products. Accordingly, the present invention may take the form of an entirely hardware embodiment, an entirely software embodiment or an embodiment combining software and hardware aspects. Furthermore, the present invention may take the form of a computer program product on a computer-usable storage medium having computer-usable program code embodied in the medium. Any suitable computer readable medium may be utilized including hard disks, CD-ROMs, optical storage devices, or magnetic storage devices.

The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

The invention is also described using flowchart illustrations and block diagrams. It will be understood that each block (of the flowcharts and block diagrams), and combinations of blocks, can be implemented by computer program instructions. These program instructions may be provided to a processor circuit, such as a microprocessor, microcontroller or other processor, such that the instructions which execute on the processor(s) create means for implementing the functions specified in the block or blocks. The computer program instructions may be executed by the processor(s) to cause a series of operational steps to be performed by the processor(s) to produce a computer implemented process such that the instructions which execute on the processor(s) provide steps for implementing the functions specified in the block or blocks.

Accordingly, the blocks support combinations of means for performing the specified functions, combinations of steps for performing the specified functions and program instruction means for performing the specified functions. It will also be understood that each block, and combinations of blocks, can be implemented by special purpose hardware-based systems which perform the specified functions or steps, or combinations of special purpose hardware and computer instructions.

Embodiments of the invention are directed to a stimulation therapy device and method for stimulating nerve branches in the tibial area of a patient, such as the S3 associated nerves. In one embodiment, the electrical stimulation therapy performed in accordance with the method delivers electrical pulses to branches of the tibial nerve to treat pelvic conditions, such as overactive bladder or urinary frequency, urinary incontinence, fecal incontinence and pelvic pain, for example. Other conditions may also be treated using the device and method.

Figure 2:
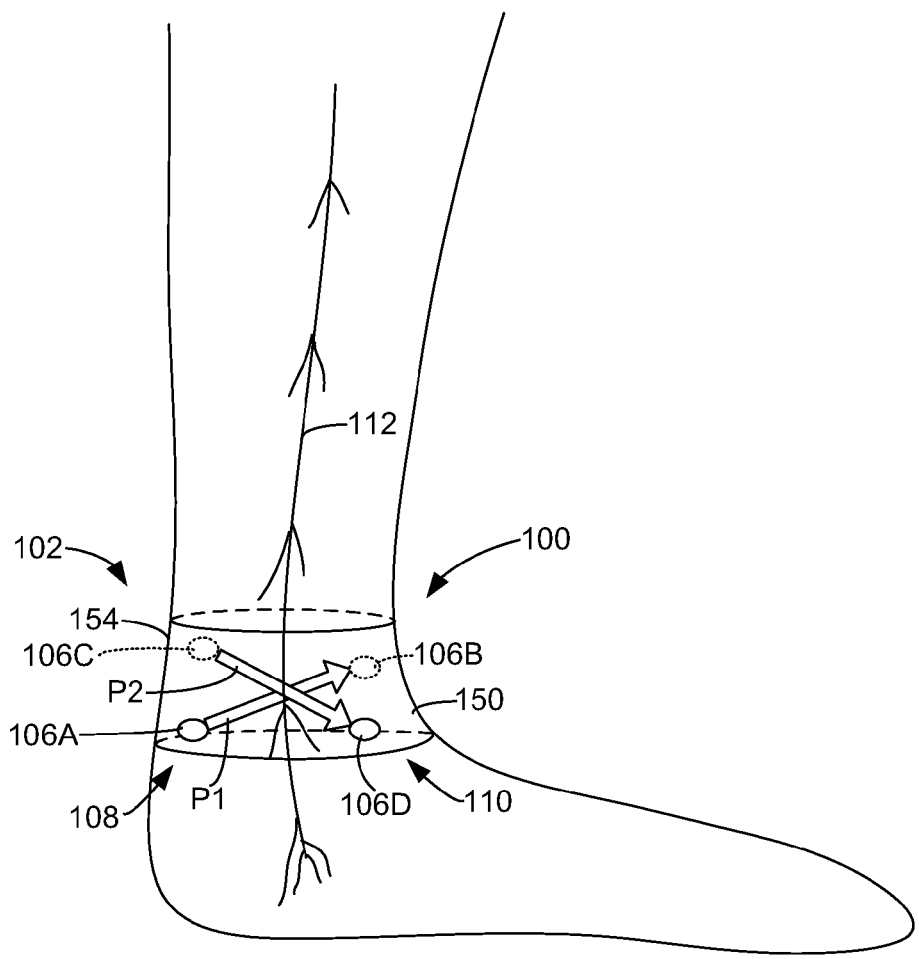
FIG. 2 is a simplified side view of a stimulation therapy device in accordance with embodiments of the invention supported around the ankle of a patient.
Figure 3:
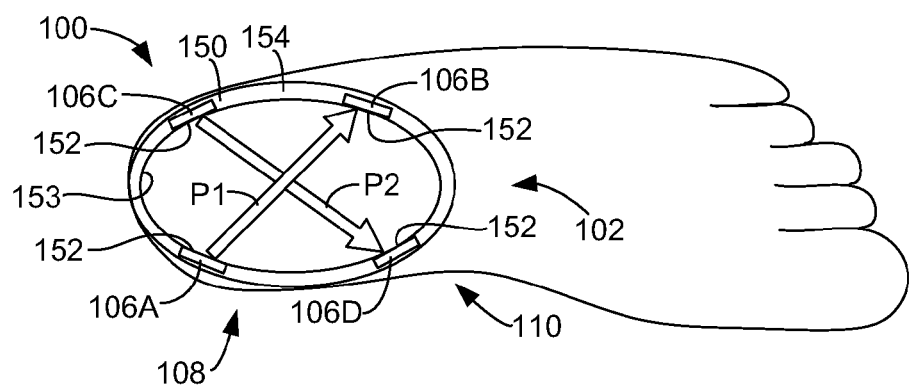
FIG. 3 is a simplified top view of the stimulation therapy device of FIG. 2.

FIG. 1 is a block diagram of a stimulation therapy device 100 in accordance with embodiments of the invention. FIG. 2 is a simplified diagram of the device 100, or a portion thereof, supported around an ankle area 102 of a patient, and FIG. 3 is a simplified top view of the stimulation therapy device 100 of FIG. 2. As used herein the "ankle area" refers to the ankle and the foot of the patient. Accordingly, as used herein, embodiments describing attaching or positioning electrodes to the ankle area of a patient include attaching or positioning electrodes on the foot of the patient.

Embodiments of the device 100 include a stimulation circuit or pulse generator 104 and electrodes 106. Embodiments of the electrodes 106 include transcutaneous surface or patch electrodes that engage the skin of the ankle area 102. In one embodiment, the surface electrodes spread the stimulation pulses over a wide physical area to minimize the generation of potentially damaging reaction products. In accordance with another embodiment, the electrodes 106 comprise one or more percutaneous needles.

In one embodiment, the electrodes 106 comprise a first pair of electrodes 108 (electrodes 106A and 106B) and a second pair of electrodes 110 (electrodes 106C and 106D), as shown in FIGS. 2 and 3. In one embodiment, the electrodes 106 of the pairs 108 and 110 are displaced from each other around the ankle area. In one embodiment, the electrodes 106A and 106B of the first pair 108 are positioned on opposing sides of the ankle 102. In one embodiment, the electrodes 106C and 106D of the second pair 110 are also positioned on opposing sides of the ankle 102, as shown in FIG. 3. In one embodiment, a plane extending through the electrodes 106A and 106B of the first pair 108 intersects a plane extending through the electrodes 106C and 106D of the second pair 110, as shown in FIG. 3.

Figure 4:
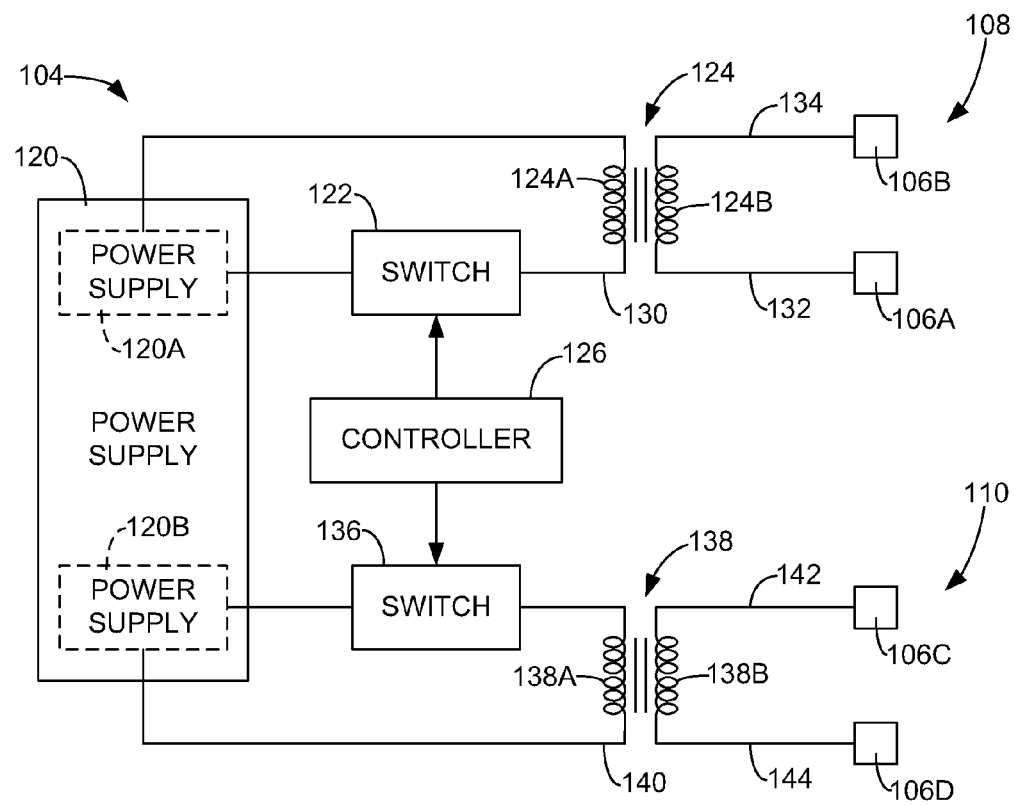
FIG. 4 is a schematic diagram of a stimulation circuit in accordance with embodiments of the invention.

FIG. 4 is a schematic diagram of the stimulation circuit 104 in accordance with embodiments of the invention. In one embodiment, the stimulation circuit 104 is configured to generate direct current electrical pulses or stimulation signals that are delivered to the tibial nerve 112 through the electrodes 106. In one embodiment, the stimulation circuit 104 is configured to deliver stimulation pulses P1 to branches of the tibial nerve 112 through the first pair of electrodes 108, and deliver stimulation pulses P2 to branches of the tibial nerve 112 through the second pair of electrodes 110, as illustrated in FIGS. 2 and 3. In one embodiment, the combination of the pulses P1 and P2 provides the desired electrical stimulation of the branches of the tibial nerve 112.

In one embodiment, the stimulation circuit 104 comprises a power supply 120, a switch 122, a transformer 124 and a controller 126. In one embodiment, the power supply 120 is a battery (e.g., 3 volt battery) or other suitable power supply. In one embodiment, the transformer 124 is a step-up transformer having a primary winding 124A and a secondary winding 124B. The transformer 124 increases the primary voltage supplied to the primary winding 124A from the power supply 120 through line 130 to a secondary voltage at the secondary winding 124B that is coupled to electrodes 106A and 106B through lines 132 and 134. In one embodiment, the primary voltage is approximately 3 volts and the secondary voltage is approximately 20-120V. In more specific embodiments, the secondary voltage is 20V or 30V. Other primary and secondary voltages may also be used.

In one embodiment, the controller 126 includes at least one processor that is configured to execute program instructions stored in memory of the controller 126, or other location, to execute functions described herein, in accordance with conventional techniques. In one embodiment, the controller 126 is configured to control the delivery of electrical pulses P1 through the electrodes 106A and 106B and tissue of the patient by controlling the flow of the current from the power supply 120 to the transformer 124 using the switch 122. The controller 126 opens the switch 122 to prevent current from flowing through the transformer 124, and closes the switch 122 to deliver current through the transformer 124. This flow of current through the transformer 124 produces a current flow or pulses P1 through the electrodes 106A and 106B when placed in contact with the ankle area 102 of the patient, as shown in FIGS. 2 and 3. Embodiments of the switch 122 include a transistor or other suitable electrical component.

The duty cycle of the stimulation pulses P1 is controlled by regulating the pulse width of the primary side of the step-up transformer 124 by actuating the corresponding switch 122 using the controller 126. In one embodiment, the electrical pulses P1 delivered to the ankle area 102 of the patient are at least partially conducted through one or more branches of the tibial nerve 112 and treat a pelvic condition of the patient.

In one embodiment, the stimulation circuit 104 includes a switch 136 and a transformer 138. In one embodiment, the transformer 138 is a step-up transformer having a primary winding 138A and a secondary winding 138B. The transformer 138 increases the primary voltage supplied to the primary winding 138A from the power supply 120 through line 140 to a secondary voltage at the secondary winding 138B that is coupled to electrodes 106C and 106D through lines 142 and 144. In one embodiment, the primary voltage is approximately 3 volts and the secondary voltage is approximately 20-120 volts. Other primary and secondary voltages, such as those mentioned above, may also be used.

In one embodiment, the controller 126 is configured to control the current to the transformer 138 from the power supply 120 through the control of the switch 136, in accordance with conventional techniques. The controller 126 opens and closes the switch 136 to produce current pulses from the power supply 120 through the line 140, which produces current pulses P2 through the electrodes 106C and 106D and the tissue of the patient, as illustrated in FIGS. 2 and 3.

The duty cycle of the stimulation pulses P2 is controlled by regulating the pulse width of the primary side of the step-up transformer 138 by actuating the corresponding switch 136 using the controller 126. In one embodiment, the electrical pulses P2 delivered to the ankle area 102 of the patient are at least partially conducted through one or more branches of the tibial nerve 112 and treat a pelvic condition of the patient.

In one embodiment, the power supply 120 includes separate power supplies 120A and 120B that are respectively configured to provide power to the portion of the stimulation circuit 104 delivering current pulses P1 and P2 to the electrode pairs 108 and 110. Alternatively, the power supply 120 may comprise a single power supply that provides electrical power to produce the pulses P1 and P2 that are delivered to the electrode pairs 108 and 110.

In one embodiment, the pulse P1 delivered to the ankle area 102 through the electrode pair 108, and the pulse P2 delivered to the ankle area 102 through the electrode pair 110 can be adjusted so that a time delay between the P1 pulse and the P2 pulse can be either positive, negative or zero. This time delay, illustrated in the stimulation pulse timing diagram (voltage over time) of FIG. 5, allows the pulses in the patient's ankle or foot to reach maximums and minimums in different locations. This effectively "steers" the electrical pulse received by the branches of the tibial nerve 112 by controlling the strength and timing of the P1 and P2 pulse vectors, shown in FIGS. 2 and 3. As a result, the time-shifted pulses P1 and P2 can be used to produce a spatial voltage in the ankle area 102 of the patient to steer a combined stimulation pulse toward the targeted tibial nerve branches of the patient.

In one embodiment, the device 100 includes a support member 150 that positions the electrode pairs 108 and 110 in the desired locations on the ankle area 102 of the patient, as shown in FIGS. 1 and 2. In one embodiment, each of the electrodes 106 includes a stimulation surface 152 that faces away from a stimulation side 153 of the support member 150 and through which the current pulses are conducted to the patient, as shown in FIG. 3. In one embodiment, the support member 150 comprises straps 154 that attach to each other to secure the device 100 to the ankle area of the patient. In one embodiment, the support member 150 is in the form of an ankle bracelet.

In one embodiment, the support member 150 includes an alignment feature that is used to position the electrodes 106 in a desired location in the ankle area of the patient. In one embodiment, the alignment feature comprises one or more apertures 156 (FIG. 1) that may be aligned with markings on the ankle area of the patient. When the markings are viewable through the apertures 152, the electrodes 106 are positioned in desired locations in the ankle area 102. In one embodiment, the markings are made on the ankle area of the patient by a physician after testing the location of the electrodes 106. This allows the patient to consistently position the electrodes relative to the ankle area 102, and allow the patient to perform stimulation treatments at home using the device 100.

In one embodiment, the support member 150 includes a mechanism configured to move the electrodes 106 toward the skin of the patient and retract the electrodes 106 from the skin of the patient. This is particularly useful when the electrodes 106 include needle electrodes. The mechanism allows the needle electrodes to be deployed into the skin of the ankle area 102 of the patient when the patient is ready for a stimulation treatment, and retract the needle electrodes when the stimulation treatment is completed.

In one embodiment, the device 100 includes a drug delivery component 158 that is configured to deliver a numbing agent to the skin of the patient. This is particularly useful when the electrodes 106 comprise needle electrodes. The numbing agent can be applied to the ankle area 102 prior to the deployment of the needle electrodes 106 to provide the patient with greater comfort.

Figure 6:
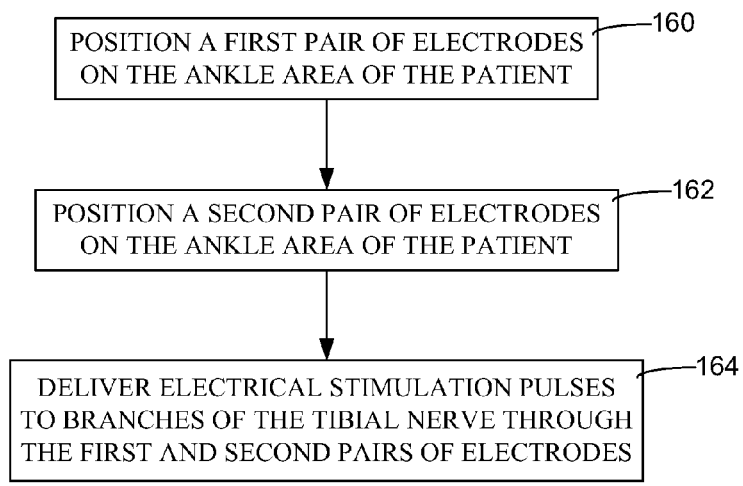
FIG. 6 is a flowchart illustrating a method of providing an electrical stimulation therapy to branches of the tibial nerve of a patient in accordance with embodiments of the invention.

FIG. 6 is a flowchart illustrating a method of providing an electrical stimulation therapy to branches of the tibial nerve 112 of a patient in accordance with embodiments of the invention. In general, the method involves the use of embodiments of the device 100 described above to apply the stimulation therapy to the ankle area 102.

At 160 of the method, a first pair of electrodes 108 is positioned on the ankle area 102 of the patient. At 162, a second pair of electrodes 110 is positioned on the ankle area 102 of the patient. Electrical stimulation pulses are then delivered to branches of the tibial nerve 112 through the first and second pairs of electrodes 108 and 110, at 164 of the method.

Embodiments of steps 160 and 162 include positioning of the pairs 108 and 110 of the electrodes 106 on opposing sides of the ankle area 102, as illustrated in FIGS. 2 and 3. In one embodiment the electrode pairs 108 and 110 are attached to a support member 150. One embodiment of the positioning steps 160 and 162 involves placing the support member 150 around the foot or ankle of the patient to place the electrode pairs 108 and 110 in contact with the ankle area 102.

In one embodiment of the method, a condition of the patient is treated responsive to step 164. Embodiments of the condition include a pelvic condition, such as overactive bladder or urinary frequency, urinary incontinence, fecal incontinence and pelvic pain.

Figure 5:
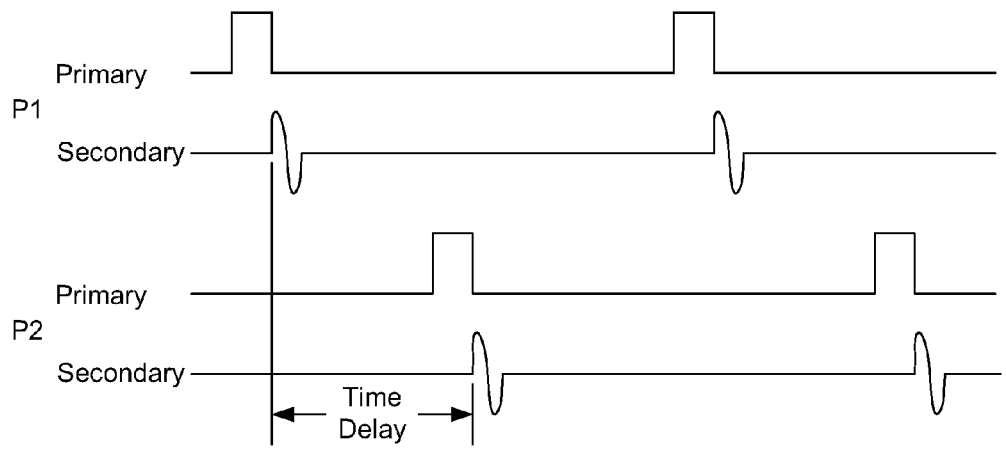
FIG. 5 is a stimulation pulse timing diagram in accordance with embodiments of the invention illustrating a voltage over time.

One embodiment of step 164 is facilitated by the stimulation circuit 104 (FIG. 4) formed in accordance with one or more embodiments described above. In one embodiment, a first stimulation pulse P1 is discharged through the first pair of electrodes 108, and a second stimulation pulse P2 is discharged through the second pair of electrodes 110. Each of the pulses P1 and P2 may represent one or more electrical pulses, such as a train of pulses. In one embodiment, the discharging of the second stimulation pulse P2 occurs after the first stimulation pulse P1 is discharged, as illustrated in FIG. 5.

In one embodiment, the pulses P1 and P2 each represents a train of pulses. In one embodiment, the pulse train P1 begins prior to the discharge of the pulse train P2. In one embodiment, the discharge of the pulse train P2 begins during the discharge of the pulse train P1. In one embodiment, the discharge of the pulse train P2 begins after the pulse train P1 has been discharged.

As discussed above, this timing of the stimulation pulses P1 and P2, as well as their voltage levels, can be used to "steer" the delivery of the stimulation therapy to the branches of the tibial nerve 112. Accordingly, adjustments to the time delay between the discharging of the pulses P1 and P2 and properties each of the pulses P1 and P2 (number of pulses in the pulse train, amplitude of the pulses, duty cycle, etc.) can be made to adjust the stimulation of the branches of the tibial nerve 112 and the stimulation treatment provided to the patient.

Although the present invention has been described with reference to preferred embodiments, workers skilled in the art will recognize that changes may be made in form and detail without departing from the spirit and scope of the invention.

What is claimed is:

1. A stimulation therapy device configured to provide an electrical stimulation therapy to branches of the tibial nerve of a patient, the device comprising:
    a support member configured to be worn around the ankle or foot of the patient;
    first and second pairs of electrodes attached to the support member, one of the second pair of electrodes is positioned between the first pair of electrodes on the support member, and one of the first pair of electrodes is positioned between the second pair of electrodes on the support member; and
    a stimulation circuit attached to the support member and configured to conduct electrical stimulation pulses through the ankle or foot to the tibial nerve of the patient through the first and second pairs of electrodes wherein the stimulation circuit comprises:
    a first stimulation pulse discharge circuit comprising:
        a first switch; and
        a first step-up transformer having a primary winding coupled to the first switch, and a secondary winding coupled to the first pair of electrodes;
    a second stimulation pulse discharge circuit comprising:
        a second switch; and
        a second step-up transformer having a primary winding coupled to the second switch, and a secondary winding coupled to the second pair of electrodes; and
    a controller configured to actuate the first and second switches between open and closed states.

2. The device of claim 1, wherein each of the electrodes has a stimulation surface that faces away from a stimulation side of the support member.

3. The device of claim 1, further comprising a power supply electrically coupled to the first switch, wherein current flows from the power supply through the first switch and through the primary winding of the first transformer when the first switch is in the closed position.

4. The device of claim 3, wherein the power supply is electrically coupled to the second switch, and current flows from the power supply through the second switch and through the primary winding of the second transformer when the second switch is in the closed position.

5. The device of claim 4, wherein the power supply comprises first and second power supplies (120A, 120B) respectively coupled to the first and second switches.

6. The device of claim 1, further comprising a drug delivery component attached to the support member.

7. The device of claim 6, wherein the drug delivery component is configured to deliver a numbing agent to the skin of the patient.

8. The device of claim 1, wherein the first and second pairs of electrodes each comprise at least one surface electrode.

9. The device of claim 1, wherein the first and second pairs of electrodes each comprise at least one needle electrode.

10. The device of claim 1, wherein the stimulation circuit conducts a first set of stimulation pulses through the ankle or foot to the tibial nerve through the first pair of electrodes, and the stimulation circuit conducts a second set of stimulation pulses through the ankle or foot to the tibial nerve through the second pair of electrodes, wherein the first and second sets of stimulation pulses are temporally offset from each other.

* * * * *